US012614631B2

(12) United States Patent
Kaneria et al.

(10) Patent No.: US 12,614,631 B2

(45) Date of Patent: Apr. 28, 2026

(54) SYSTEMS AND METHODS TO PROCESS A HEALTHCARE TRANSACTION IN A HETEROGENEOUS ENVIRONMENT COMPRISED OF MAINFRAME AND CLOUD BASED SYSTEMS IN REAL-TIME

(71) Applicant: Evernorth Strategic Development, Inc., St. Louis, MO (US)

(72) Inventors: Ankur Kaneria, Cedar Park, TX (US); Harry S. Gangaikondan-Iyer, Morris Plains, NJ (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 274 days.

(21) Appl. No.: 17/945,300

(22) Filed: Sep. 15, 2022

(65) Prior Publication Data

US 2023/0215549 A1     Jul. 6, 2023

Related U.S. Application Data

(60) Provisional application No. 63/295,622, filed on Dec. 31, 2021.

(51) Int. Cl.
| | |
|---|---|
| *G16H 40/20* | (2018.01) |
| *G06Q 40/08* | (2012.01) |
| *G06Q 50/22* | (2024.01) |

(52) U.S. Cl.
CPC ............. *G16H 40/20* (2018.01); *G06Q 40/08* (2013.01); *G06Q 50/22* (2013.01)

(58) Field of Classification Search
CPC ......... G16H 40/20; G06Q 40/08; G06Q 50/22
See application file for complete search history.

(56) References Cited

U.S. PATENT DOCUMENTS

| | | | |
|---|---|---|---|
| 9,619,841 B2 * | 4/2017 | DiRienzo | ............... G06Q 40/08 |
| 10,664,572 B2 | 5/2020 | Bitran | |

(Continued)

FOREIGN PATENT DOCUMENTS

| | | | | |
|---|---|---|---|---|
| CN | 114783577 A | * | 7/2022 | ......... G06Q 30/0203 |

OTHER PUBLICATIONS

Zhou et al., "Big Data-Driven Abnormal Behavior Detection in Healthcare Based on Association Rules," Jul. 13, 2020, IEEE Access, pp. 129002-129011. (Year: 2020).*

*Primary Examiner* — Kenneth Bartley

(74) *Attorney, Agent, or Firm* — Dickinson Wright PLLC

(57) ABSTRACT

A method performed by a system for processing healthcare transactions is disclosed herein. The method comprises: receiving, by the cloud computing platform and the mainframe platform, a request for coverage of a service received by a member under a health insurance plan; assessing, by the mainframe platform, coverage of the service under the health insurance plan; determining, by the cloud computing platform, a first and a second healthcare attribute associated with the service; receiving, by the mainframe platform, the first healthcare attribute and the second healthcare attribute; and generating, by the mainframe platform, a response to the request for coverage of the service under the health insurance plan indicating the value associated with the second healthcare attribute, wherein the response is generated in response to a value associated with the first healthcare attribute being greater than a value associated with the second healthcare attribute.

16 Claims, 10 Drawing Sheets

(56)                    References Cited

U.S. PATENT DOCUMENTS

| | | | | |
|---|---|---|---|---|
| 10,713,287 | B1 * | 7/2020 | Rosomoff | G06F 16/332 |
| 10,733,683 | B2 | 8/2020 | Kapur | |
| 10,776,890 | B1 | 9/2020 | Samarin | |
| 10,810,223 | B2 | 10/2020 | Sundararaman | |
| 10,839,949 | B1 * | 11/2020 | Hutchison | G16H 10/60 |
| 10,853,453 | B1 * | 12/2020 | Littlecreek | G16H 40/20 |
| 11,170,394 | B1 * | 11/2021 | Macinski | G16H 20/10 |
| 11,361,381 | B1 | 6/2022 | Lehmuth | |
| 11,515,022 | B1 * | 11/2022 | Dey | G16H 40/20 |
| 2005/0091080 | A1 | 4/2005 | Biats, Jr. | |
| 2005/0251428 | A1 | 11/2005 | Dust | |
| 2006/0149603 | A1 | 7/2006 | Patterson | |
| 2007/0011449 | A1 * | 1/2007 | DiRienzo | G06Q 10/00 |
| | | | | 713/153 |
| 2007/0203757 | A1 | 8/2007 | Dibiasi | |
| 2007/0260493 | A1 * | 11/2007 | DiRienzo | G06Q 99/00 |
| | | | | 705/4 |
| 2008/0010096 | A1 | 1/2008 | Patterson | |
| 2009/0164243 | A1 | 6/2009 | Zubak | |
| 2010/0324936 | A1 | 12/2010 | Vishnubhatla | |
| 2011/0288881 | A1 | 11/2011 | Machani | |
| 2014/0067415 | A1 | 3/2014 | Mun | |
| 2014/0297304 | A1 | 10/2014 | Nguyen | |
| 2014/0337058 | A1 | 11/2014 | Sullivan | |
| 2015/0088560 | A1 * | 3/2015 | DiRienzo | G06Q 40/08 |
| | | | | 705/4 |
| 2016/0093010 | A1 | 3/2016 | Vasiliu-Feltes | |
| 2016/0350501 | A1 | 12/2016 | Rothschild | |
| 2017/0083673 | A1 | 3/2017 | Dawson, III | |
| 2020/0043035 | A1 * | 2/2020 | Peysekhman | G06Q 40/08 |
| 2020/0167871 | A1 | 5/2020 | Basu | |
| 2020/0234379 | A1 * | 7/2020 | Geylani | G06Q 10/067 |
| 2022/0051276 | A1 * | 2/2022 | Zelocchi | G16H 30/40 |
| 2023/0289889 | A1 * | 9/2023 | Greenblatt | G06Q 40/08 |

* cited by examiner

112

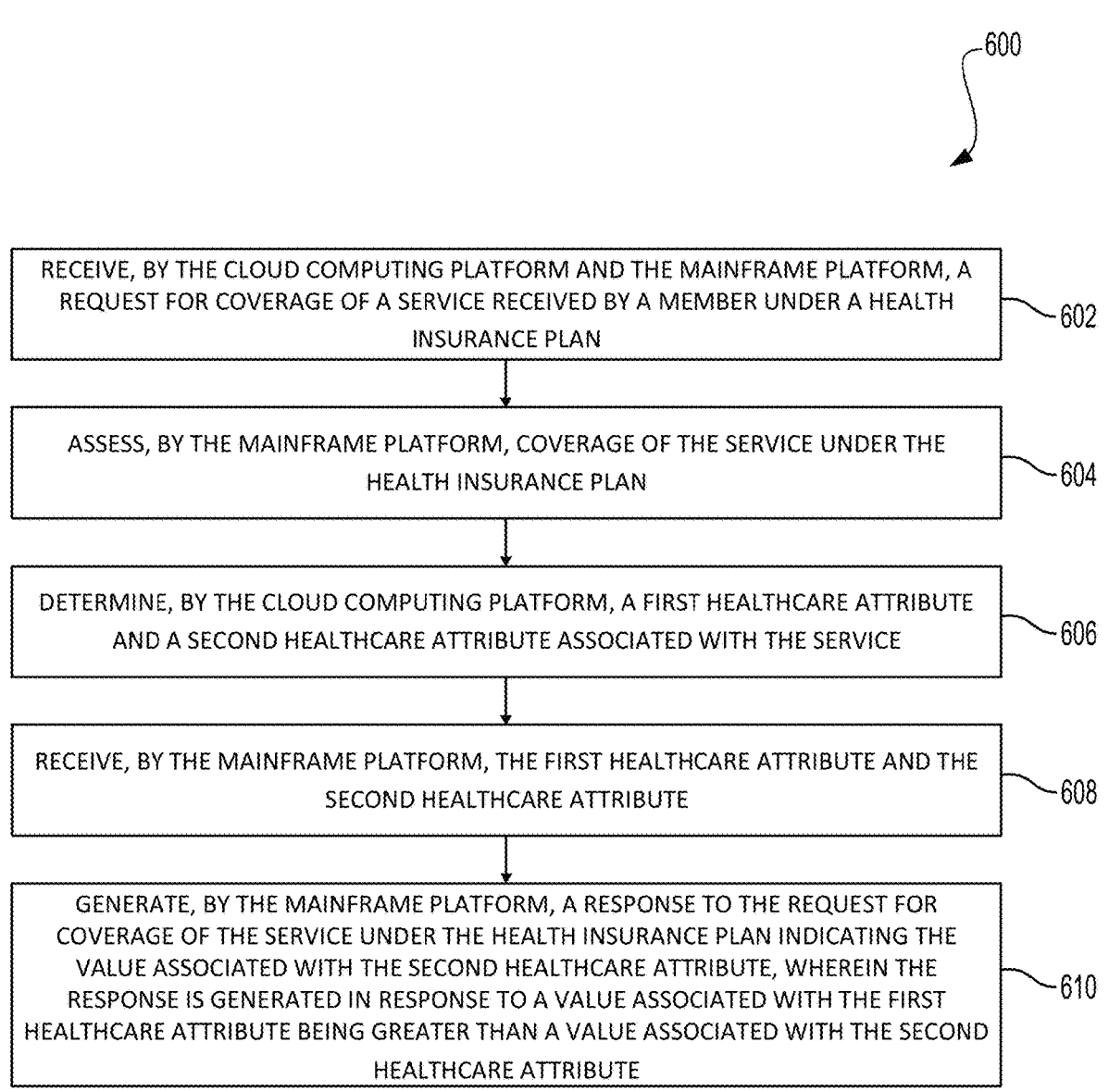

RECEIVE, BY THE CLOUD COMPUTING PLATFORM AND THE MAINFRAME PLATFORM, A REQUEST FOR COVERAGE OF A SERVICE RECEIVED BY A MEMBER UNDER A HEALTH INSURANCE PLAN ~602

ASSESS, BY THE MAINFRAME PLATFORM, COVERAGE OF THE SERVICE UNDER THE HEALTH INSURANCE PLAN ~604

DETERMINE, BY THE CLOUD COMPUTING PLATFORM, A FIRST HEALTHCARE ATTRIBUTE AND A SECOND HEALTHCARE ATTRIBUTE ASSOCIATED WITH THE SERVICE ~606

RECEIVE, BY THE MAINFRAME PLATFORM, THE FIRST HEALTHCARE ATTRIBUTE AND THE SECOND HEALTHCARE ATTRIBUTE ~608

GENERATE, BY THE MAINFRAME PLATFORM, A RESPONSE TO THE REQUEST FOR COVERAGE OF THE SERVICE UNDER THE HEALTH INSURANCE PLAN INDICATING THE VALUE ASSOCIATED WITH THE SECOND HEALTHCARE ATTRIBUTE, WHEREIN THE RESPONSE IS GENERATED IN RESPONSE TO A VALUE ASSOCIATED WITH THE FIRST HEALTHCARE ATTRIBUTE BEING GREATER THAN A VALUE ASSOCIATED WITH THE SECOND HEALTHCARE ATTRIBUTE ~610

FIG. 6

SYSTEMS AND METHODS TO PROCESS A HEALTHCARE TRANSACTION IN A HETEROGENEOUS ENVIRONMENT COMPRISED OF MAINFRAME AND CLOUD BASED SYSTEMS IN REAL-TIME

CROSS REFERENCE TO RELATED APPLICATIONS

This application claims the benefit of U.S. Provisional Application No. 63/295,622, filed Dec. 31, 2021, the entire disclosure of which is incorporated by reference.

TECHNICAL FIELD

This disclosure relates to systems and methods for processing a healthcare transaction in a heterogeneous environment, e.g., including mainframe and cloud based systems.

BACKGROUND

Individuals spend a large amount on healthcare every year, and the cost keeps rising. For example, each year, there are substantial increases in the prices of drugs. The affordability of prescription drugs is a key consideration in patient care. To combat the rising prices of drugs, prescription discount cards are available for use at pharmacies nationwide. The vendors that provide these discount programs negotiate deals with the pharmaceutical industry to provide a cheaper solution for obtaining drugs.

SUMMARY

This disclosure relates generally to heterogeneous computing within a single environment to increase speed and accuracy of data analysis. The heterogeneous computing can include a mainframe computing system to provide linear rule based computing and a distributed computing system(s) that apply a model to each incoming data set, e.g., a claim record. The model can be prepared using a predictive model engine being applied to the historical processing of claim records.

An aspect of the disclosed embodiments includes a system for processing a number of data records, e.g., healthcare transactions, healthcare claims or other successive data records, which are significant in number (e.g., over tens of thousands or millions per day) and require fast decisions (e.g., one second or less, one to two seconds, seconds, and less than ten seconds). The system comprises a cloud computing platform that includes at least a first processor and at least a first memory. In an example, the first memory includes instructions that, when executed by the first processor, cause the first processor to: receive a request for first data processing related to a member under a specific rule set (e.g., out of a rule set that is larger than the specific rule set); determine a first attribute and a second attribute associated with service under the specific rule set; and store the first attribute and the second attribute. The system can also comprise a mainframe platform comprising a second processor and a second memory. The second memory includes instructions that, when executed by the second processor, cause the second processor to: for first data processing related to a member under a specific rule set (e.g., out of a rule set that is larger than the specific rule set); assess a specific rule set to be applied to the first data processing; receive the first attribute and the second attribute; and in response to a value associated with the first attribute being greater than a value associated with the second attribute, generate a response from the first data processing indicating the value associated with the second attribute.

In an example, the first memory includes instructions that, when executed by the first processor, cause the first processor to: receive a request for first data processing, e.g., coverage of a service received by a member under a health insurance plan; determine a first and a second healthcare attribute associated with the service; and store the first healthcare attribute and the second healthcare attribute. The system can also comprise a mainframe platform comprising a second processor and a second memory. The second memory includes instructions that, when executed by the second processor, cause the second processor to: receive the request for coverage of the service received by the member under the health insurance plan; assess coverage of the service under the health insurance plan; receive the first healthcare attribute and the second healthcare attribute; and in response to a value associated with the first healthcare attribute being greater than a value associated with the second healthcare attribute, generate a response to the request for coverage of the service under the health insurance plan indicating the value associated with the second healthcare attribute.

Another aspect of the disclosed embodiments includes a method performed by a system for processing healthcare data processes, e.g., transactions, records processing, rectifying health data and the like. The system comprises a cloud computing platform and a mainframe platform. The method comprises: receiving, by the cloud computing platform and the mainframe platform, a request for coverage of a service received by a member under a health insurance plan; assessing, by the mainframe platform, coverage of the service under the health insurance plan; determining, by the cloud computing platform, a first and a second healthcare attribute associated with the service; receiving, by the mainframe platform, the first healthcare attribute and the second healthcare attribute; and generating, by the mainframe platform, a response to the request for coverage of the service under the health insurance plan indicating the value associated with the second healthcare attribute, wherein the response is generated in response to a value associated with the first healthcare attribute being greater than a value associated with the second healthcare attribute.

Another aspect of the disclosed embodiments includes a system for processing data transactions. The system comprises a cloud computing platform that includes at least a processor and at least a first memory. The first memory including instructions that, when executed by the processor, cause the processor to: receive a request for data processing associated with a member under a rule set from a plurality of rules; determine whether the mainframe platform has access to attributes associated with the rule set; and in response to determining the mainframe platform does not have access to attributes associated with the rule set: determine the first attribute and the second attribute associated with the rule set; and store the first attribute and the second attribute in a data store for a mainframe platform to access for generating a response from the data processing.

Another aspect of the disclosed embodiments includes a system for processing healthcare transactions. The system comprises a cloud computing platform that includes at least a processor and at least a first memory. The first memory including instructions that, when executed by the processor, cause the processor to: receive a request for coverage of a service received by a member under a health insurance plan; determine whether the mainframe platform has access to attributes associated with the service; and in response to determining the mainframe platform does not have access to attributes associated with the service: determine the first and the second healthcare attribute associated with the service; and store the first healthcare attribute and the second health-care attribute in a data store for a mainframe platform to access for generating a response to the request for coverage of the service.

These and other aspects of the present disclosure are disclosed in the following detailed description of the embodiments, the appended claims, and the accompanying figures.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 6 is a flow diagram generally illustrating a method for processing healthcare transactions according to the principles of the present disclosure.

DETAILED DESCRIPTION

Figure 1A:
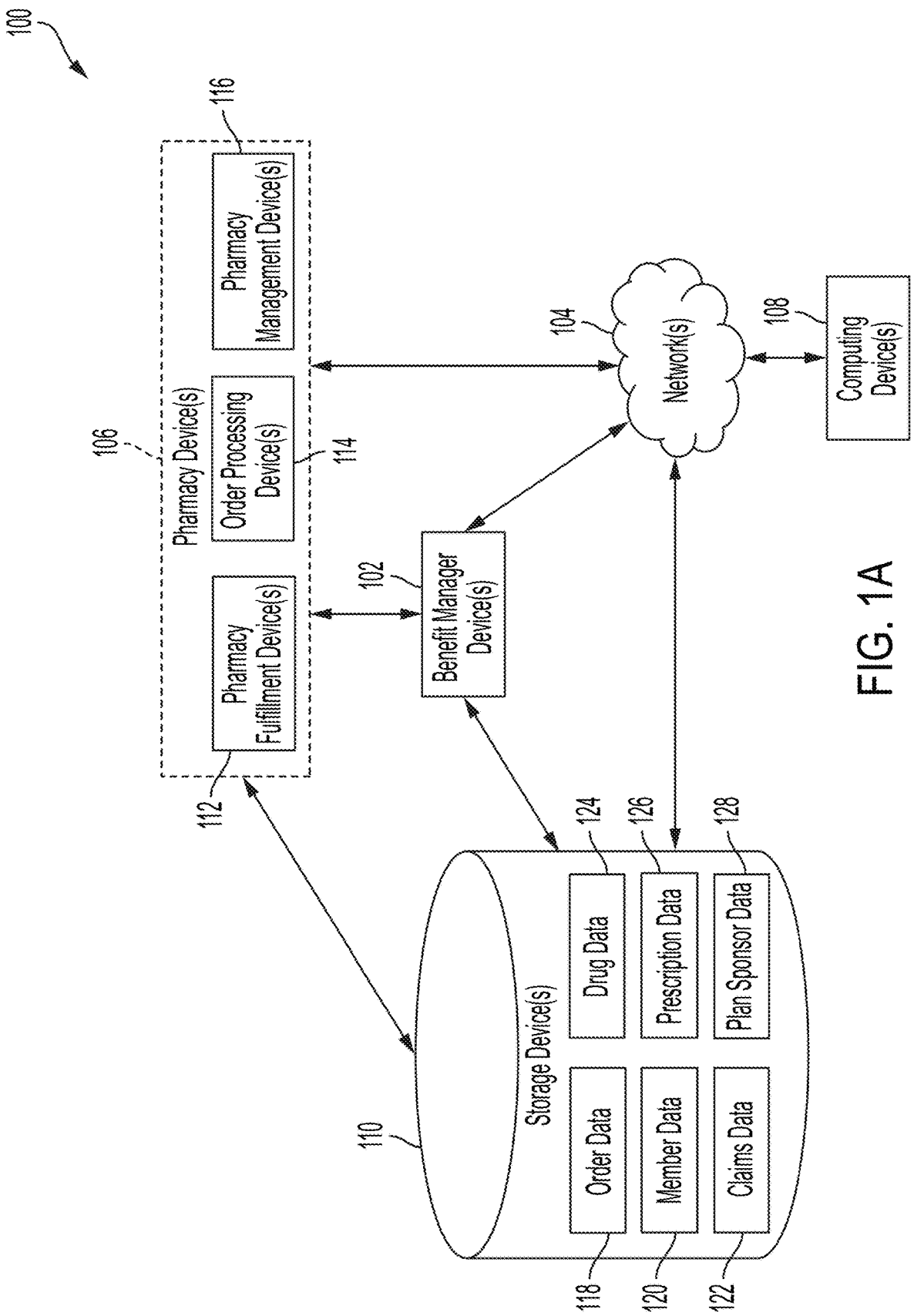
FIG. 1A generally illustrates a functional block diagram of a system including a high-volume pharmacy according to the principles of the present disclosure.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As described, individuals spend a large amount on health-care every year, and the cost keeps rising. For example, each year, there are substantial increases in the prices of drugs.

The affordability of prescription drugs is a key consideration in patient care. To combat the rising prices of drugs, prescription discount cards are available for use at pharmacies nationwide. The vendors that provide these discount programs negotiate deals with the pharmaceutical industry to provide a cheaper solution for obtaining drugs. However, the use of these discount cards may result in a lack of drug utilization review, drug interaction review, accuracy of treatment databases and the like. The member may not receive the full benefits of their healthcare plan. The accuracy of the healthcare databases provides a basis for greater insights into healthcare, e.g., identification of predictive models. Predictive models may improve health outcomes, identify inefficiencies, and reduce fraud waste and abuse. The health-care database can also identify adherence issues. The decisions using data processing related to healthcare must be made timely; however, the rule sets for making these decisions continue to grow in quantity and complexity while the number of decisions also continues to grow. Accordingly, the inventors of the present disclosure identified a need to increase the speed of arriving at decisions related to applying rule sets to specific data processing requests related to individual member records. It is believed that the non-bifurcation of the data processing would impose a time increase of over 400% relative to the presently described processes and structures. In the drug adjudication application of the present disclosure, using a single mainframe architecture would result in an additional 53% to the processing time. In a simulation of one architecture of the present disclosure, a single data processing transaction took approximately two seconds. In a traditional methodology in a single mainframe environment, the processing using multiple attributes took approximately three seconds. Over the course of handling tens of thousands of data processing transactions per hour, the increase in processing time can result in bottlenecks that delay processing of subsequent data processing requests, or some data processing requests being faulted out of the system. It is believed that the present processing system can reduce data processing times to less than one second, one to two seconds or similar shortened processing times, e.g., to half or less time compared to prior single computing systems performing similar tasks.

The present description allows the system to quickly and accurately extrapolate any parametric combination. An algorithm and system architecture as described herein can build a processing database from identifying the attributes of a record and building parametric combinations of the subject matter of the records. The parametric combination can be in 1 to N dimensions, with N being the number of identified attributes from the data records. The system can perform static calculations on the dimensions of the attributes. In an example, a drug record may have one to five attributes, e.g., drug identifier (e.g., national drug code, drug name or the like), dosages for that drug, a combination of other drugs likely to be combined with that drug and the potential filling pharmacy. In an example, the drug dosage may include sub-attributes of a number of individual doses and the drug strength of those doses. The sub-attributes can be combined to generate a single attribute for a specific version (quantity and dosage) of a particular drug, e.g., its individual record. Using these attributes, a parametric combination database inclusive of generated records can be created using the present systems. The present systems and methods can perform a multiplicative action of the attributes to generate the parametric combination. It is within the scope of the present disclosure to perform other operations to generate the parametric combination.

For example, when a member goes to a pharmacy to get a prescription, the member may compare the healthcare plan price (i.e., what is the cost of the drug based upon the healthcare insurance plan) to any discount card price that is available. If the discount price is cheaper, the member will take the drug through the discounted program.

To keep members within the healthcare plan (i.e., not using discount cards or programs outside of a health plan for healthcare services), members will need to be provided more competitive prices for healthcare services under their health insurance plan. For example, during adjudication of a pharmacy claim, a health insurance provider may compare a price of the drug under a health insurance plan to a price of the drug without using insurance. The health insurance provider may then respond to a request for coverage of the drug with the lowest price. However, this process may increase the adjudication time of the health insurance claim. The member staying within the healthcare plan may provide certain benefits to the health of the patient, e.g., a thorough drug utilization review, checking for drug interactions, conducting fraud, waste and abuse review.

Conventionally, the adjudication of health insurance claims occurs only on a mainframe. A mainframe is a large computer platform designed to process very large amounts of data quickly. Mainframe systems are widely used in industries like the healthcare sector, financial sector, airline reservations, logistics and other fields where a large number of transactions need to be processed as part of routine business practices. During the adjudication of a health insurance claim, a mainframe platform may check the eligibility of a member under the health insurance plan and compare the health insurance plan benefits to the services received by the member. Further, based on the health insurance plan details, the claim is adjudicated to identify if the health insurance plan covers each service in a claim and how much is covered by the health insurance plan and what the member will owe for the service.

Embodiments described herein are directed to a mechanism to leverage mainframe and cloud technologies to process real-time healthcare transactions, like health insurance claims, in a hybrid fashion. The system is built with parallel processing where cloud and mainframe engines pick up the same transaction but start working on different parts of the claims and towards the end of the claim adjudication process, bring the transaction together for a final response to the claim. This parallel processing achieves the same or better results (e.g., accuracy) than conventional data record processing of claims, while reducing record approval times, e.g., two seconds or less, one second, or less than one second.

For example, in the context of pharmacy claims adjudication, a claim is received by both the mainframe platform and the cloud platform. In parallel, while the mainframe is doing the necessary coverage checks (e.g., determining eligibility of a member under the health insurance plan, determining if a healthcare service is covered by the healthcare plan, etc.), the cloud platform completes the pricing aspects of the claim processing. Any pricing calculations are then stored in a database by the cloud platform and the mainframe platform receives the pricing calculations and determines a response to the claim based on the pricing calculations. That is the pricing calculations run in parallel on a different computing system than the health and safety computations being run on a same data record related to a single member for a single member.

Some benefits of the embodiments described herein include enabling health insurance providers to prevent the loss of members' business to a discount program and further discourage members from shopping around for drugs as the health insurance provider provides competitive prices for drugs. Another benefit of the embodiments described herein include enabling health insurance providers to retain that visibility to drug trends of its members. This information is vital in negotiating contracts for drugs with pharmaceutical companies. Embodiments described herein further bestow benefits to members of health insurance plans. For example, the benefits include allowing for drug utilization review and members to contribute to accumulators for their health insurance plans.

FIG. 1A is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, or alternatively, in some embodiments, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
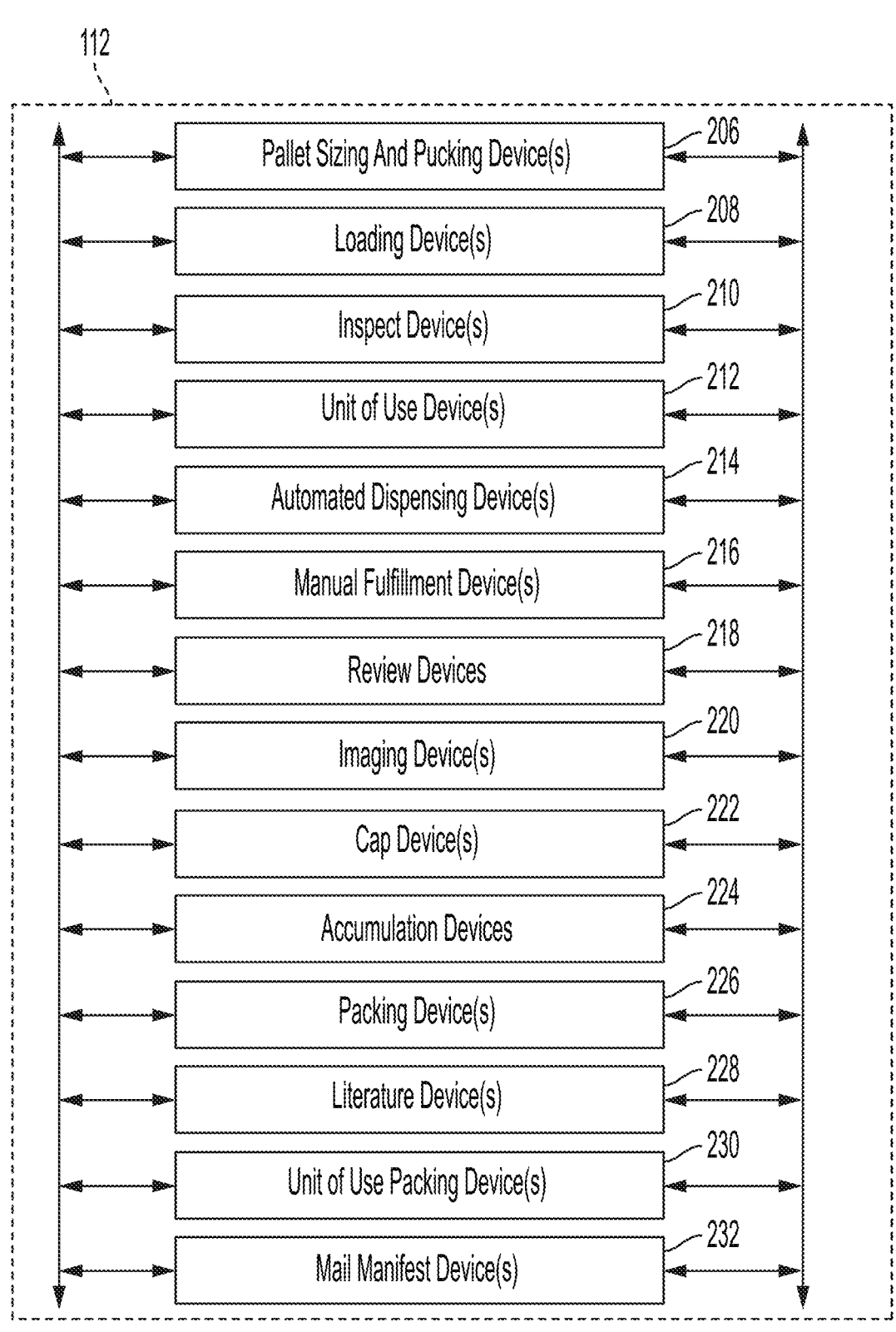
FIG. 2 generally illustrates a functional block diagram of a pharmacy fulfillment device, which may be deployed within the system of FIG. 1A.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
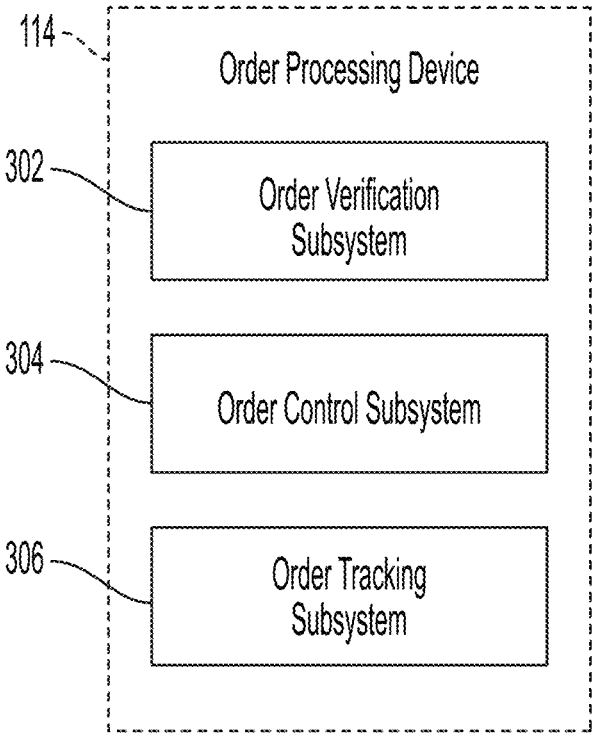
FIG. 3 generally illustrates a functional block diagram of an order processing device, which may be deployed within the system of FIG. 1A.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, and the like. The order tracking subsystem 306 may store data locally (for example, in a memory) or as a portion of the order data 118 stored in the storage device 110.

Figure 1B:
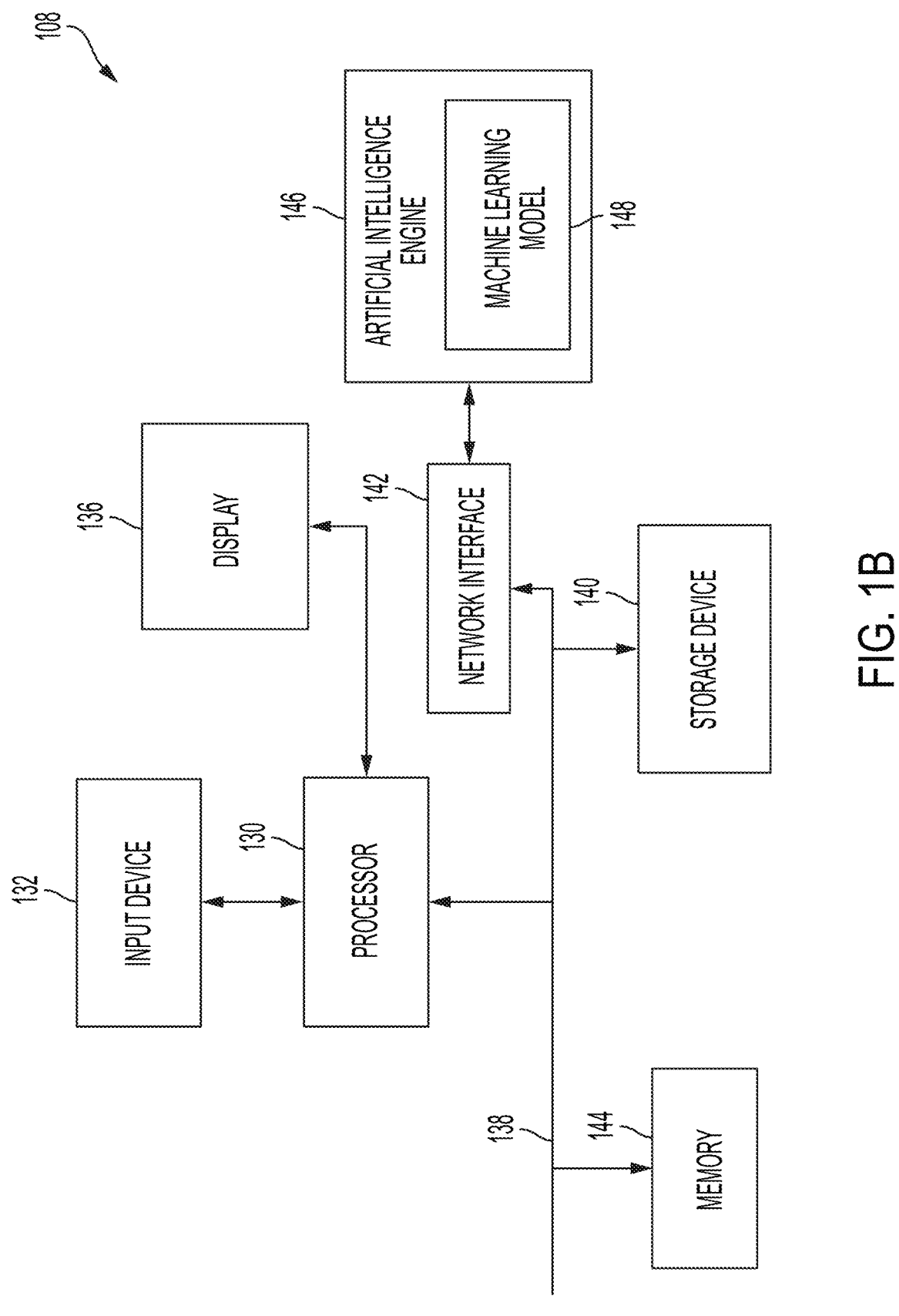
FIG. 1B generally illustrates a computing device according to the principles of the present disclosure.

In some embodiments, the system 100 may include one or more computing devices 108, as is generally illustrated in FIG. 1B. The computing device 108 may include any suitable computing device, such as a mobile computing device, a desktop computing device, a laptop computing device, a server computing device, other suitable computing device, or a combination thereof. The computing device 108 may be used by a user accessing the pharmacy associated with the system 100, as described. Additionally, or alternatively, the computing device 108 may be configured to identify an optimum or substantially optimum combination of data objects, as described.

The computing device 108 may include a processor 130 configured to control the overall operation of computing device 108. The processor 130 may include any suitable processor, such as those described herein. The computing device 108 may also include a user input device 132 that is configured to receive input from a user of the computing device 108 and to communicate signals representing the input received from the user to the processor 130. For example, the user input device 132 may include a button, keypad, dial, touch screen, audio input interface, visual/image capture input interface, input in the form of sensor data, etc.

The computing device 108 may include a display 136 that may be controlled by the processor 130 to display information to the user. A data bus 138 may be configured to facilitate data transfer between, at least, a storage device 140 and the processor 130. The computing device 108 may also include a network interface 142 configured to couple or connect the computing device 108 to various other computing devices or network devices via a network connection, such as a wired or wireless connection, such as the network 104. In some embodiments, the network interface 142 includes a wireless transceiver.

The storage device 140 may include a single disk or a plurality of disks (e.g., hard drives), one or more solid-state drives, one or more hybrid hard drives, and the like. The storage device 140 may include a storage management module that manages one or more partitions within the storage device 140. In some embodiments, storage device 140 may include flash memory, semiconductor (solid state) memory or the like. The computing device 108 may also include a memory 144. The memory 144 may include Random Access Memory (RAM), a Read-Only Memory (ROM), or a combination thereof. The memory 144 may store programs, utilities, or processes to be executed in by the processor 130. The memory 144 may provide volatile data storage, and stores instructions related to the operation of the computing device 108.

In some embodiments, the processor 130 may be configured to execute instructions stored on the memory 144 to, at least, perform the systems and methods described herein. For example, the processor 130 may be configured to receive a request for coverage of a service received by a member under a health insurance plan, determine eligibility of the member under the health insurance plan, and determine if the service is covered by the health insurance plan. The processor 130 may be further configured to determine a first healthcare attribute and a second healthcare attribute associated with the service and generate a response to the request for coverage of the service under the health insurance plan indicating a value associated with the second healthcare attribute. The response may be generated in response to a value associated with the first healthcare attribute being greater than a value associated with the second healthcare attribute. As used herein, healthcare attributes may refer to any attributes associated with a requested healthcare service. For example, the healthcare attributes may include patient information (e.g., patient's name, gender, etc.), information related to the service (e.g., diagnosis code, place of service, date of service, service code, etc.), and health insurance information (e.g., subscriber identification number or plan number).

Figure 4:
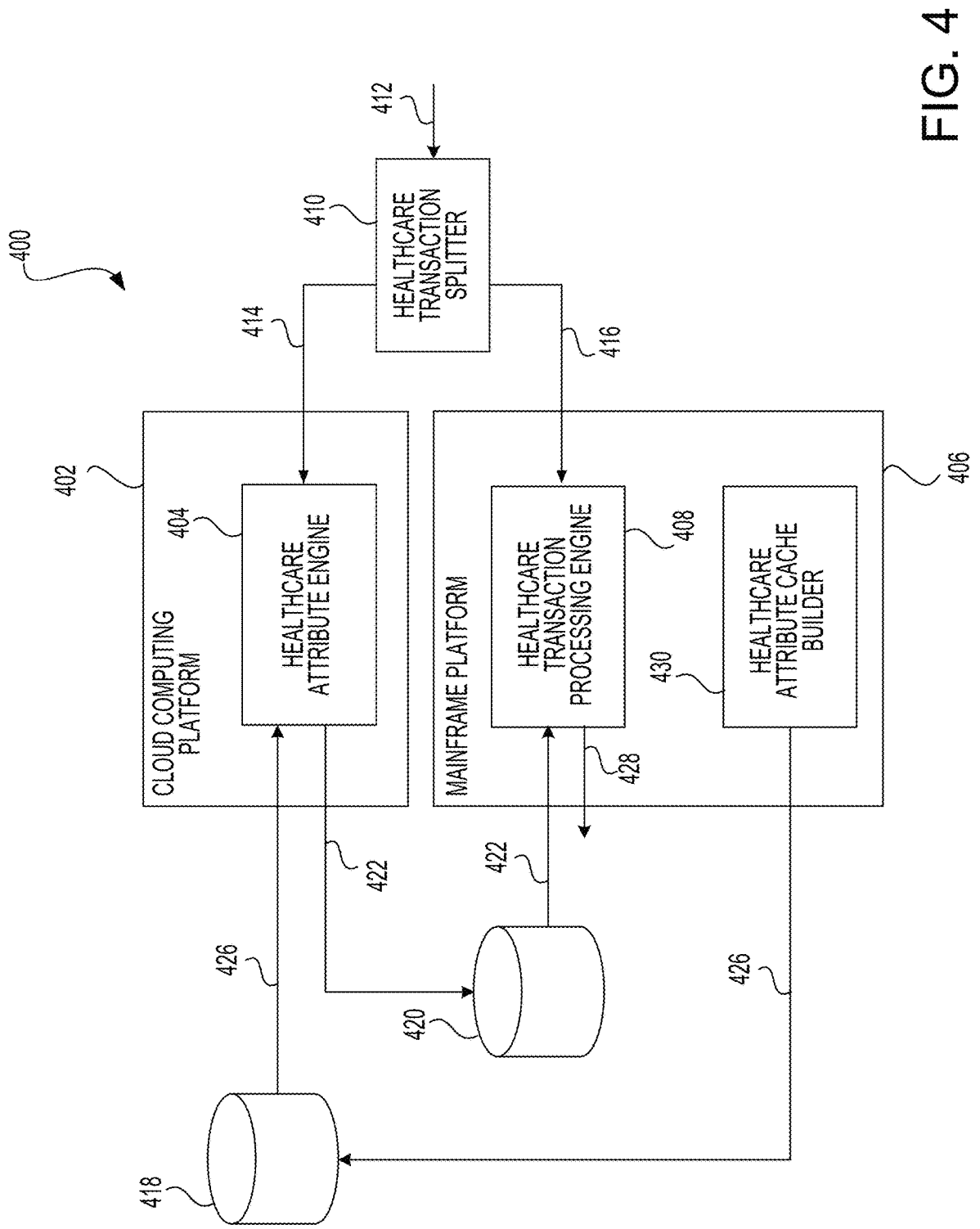
FIG. 4 generally illustrates a functional block diagram of a system for processing healthcare transactions according to the principles of the present disclosure.

To help explore the foregoing in more detail, FIG. 4 will now be described. FIG. 4 is a block diagram of an example implementation of a system 400 for processing healthcare transactions. While the system 400 will namely be described within the context of pharmacy claims adjudication, the system 400 and/or components of the system 400 may otherwise be deployed for processing other healthcare transactions (e.g., parallel drug utilization review, price review of different insurance plans, etc.). In accordance with embodiments described herein, select workloads may be performed on the cloud computing platform rather than on the mainframe platform such that aspects of the healthcare transaction can be processed in parallel. As shown in FIG. 4, system 400 includes a cloud computing platform 402, a mainframe platform 406, a healthcare transaction splitter 410, and storage devices 418 and 420. As further shown in FIG. 4, cloud computing platform 402 includes a healthcare attribute engine 404, and mainframe platform 406 includes a healthcare transaction processing engine 408 and a healthcare attribute cache builder 430.

Healthcare transaction splitter 410 may be configured to receive a healthcare transaction 412 and provide data 416 associated with healthcare transaction 412 to healthcare transaction processing engine 408 and data 414 associated with healthcare transaction 412 to healthcare attribute engine 404. For example, healthcare transaction 412 may include a health insurance claim requesting coverage of a healthcare service (e.g., for dental care, a doctor visit, laboratory and diagnostic care, etc.) provided to a member under a health insurance plan. More specifically, in the context of adjudicating pharmacy claims, healthcare transaction splitter 410 may receive a pharmacy claim requesting coverage of a drug for a member under the healthcare plan and provide the pharmacy claim or certain attributes (e.g., information for the drug, pharmacy, quantity, and day supply) of the pharmacy claim to healthcare transaction processing engine 408 and healthcare attribute engine 404.

In FIG. 4, healthcare transaction processing engine 408 may be configured to receive data 416 associated with healthcare transaction 412 and process data 416 to assess coverage of the service under the health insurance plan. To help further illustrate, and with continued reference to the example described above, healthcare transaction processing engine 408 may be configured to receive the pharmacy claim and assess coverage of a drug under the health insurance plan (e.g., verifying eligibility for the member, performing a drug utilization review (DUR) for the member, etc.).

Further, healthcare attribute engine 404 may be configured to receive data 414 associated with healthcare transaction 412 and process data 414 to determine one or more healthcare attributes associated with a service received by member of a health insurance plan. To help illustrate, and with continued reference to the example described above, healthcare attribute engine 404 may receive a pharmacy claim requesting coverage of a drug for a member under a health insurance plan and determine one or more pricing attributes associated with filling the prescription for the drug. For example, the pricing attributes may include a price for filling the prescription under the health insurance plan ("plan price") and a price for filling the prescription without using the health insurance plan ("cash price"). In some embodiments, healthcare attribute engine 404 may be responsible for performing the pricing aspect of the pharmacy claim adjudication in parallel with the necessary health insurance coverage checks performed by healthcare transaction processing engine 408.

In some embodiments, healthcare attribute engine 404 may be configured to perform the drug utilization review of the pharmacy claim adjudication in parallel with the necessary health insurance coverage checks performed by healthcare transaction processing engine 408. For example, healthcare attribute engine 404 may compare a drug and a prescription drug dosage and directions with patient information for possible drug interactions or duplicate therapy. Healthcare attribute engine 404 and/or healthcare transaction processing engine 408 may be configured to process any aspect of a healthcare claims adjudication. Further, healthcare attribute engine 404 and healthcare transaction processing engine 408 may be configured to process in parallel different aspects of healthcare claims adjudication.

Additionally, or alternatively, healthcare attribute engine 404 may include a machine learning (ML) model generator and ML models. The ML model generator may be configured to generate the ML models to facilitate determining one or more healthcare attributes associated with a service. The ML models may be deployed in healthcare attribute engine 404.

In some embodiments, the ML model generator may be configured to generate a healthcare attribute association model that generates one or more predictions indicating associations between healthcare attributes. For example, the model generator includes a machine learning algorithm. Machine learning algorithm may be provided with healthcare attributes associated with previous requests for healthcare services as input and is executed by model generator to generate the healthcare attribute association model. The healthcare attribute association model may generate predictions indicating associations between healthcare attributes associated with healthcare services. Some healthcare attributes may include patient information (e.g., gender, occupation, age, location, etc.), information related to the service (e.g., diagnosis code, place of service, date of service, service code, etc.), and health insurance information (e.g., subscriber identification number or plan number, deductible, insurance type, etc.). Some services may include requests for medical, surgical, dental, x-ray, ambulance, hospital, professional nursing medical, surgical, dental, x-ray, ambulance, hospital, and professional nursing services and may also include cost of eyeglasses, hearing aids, pharmaceuticals, orthopedics, and prosthetic devices.

Additionally, or alternatively, ML model generator may also include a ML application that implements the ML algorithm to the healthcare attribute association model. When the ML algorithm is implemented, it may find patterns between the healthcare attributes to map the healthcare attributes to each other, and output a model that captures the associations between healthcare attributes. The healthcare attributes model may be generated using any suitable techniques, including supervised machine learning model generation algorithms such as supervised vector machines (SVM), linear regression, logistic regression, naïve Bayes, linear discriminant analysis, decision trees, k-nearest neighbor algorithm, neural networks, recurrent neural network, etc. In some embodiments, unsupervised learning algorithms may be used such as clustering or neural networks.

Note that the healthcare attributes model may be generated in various forms. In accordance with some embodiments, the healthcare attributes model may be generated according to a suitable machine-learning algorithm mentioned elsewhere herein or otherwise known. In some embodiments, the ML model generator may implement a gradient boosted tree algorithm or other decision tree algorithm to generate and/or train the healthcare attributes model in the form of a decision tree. The decision tree may be traversed with input data (information related to the request for a healthcare service, etc.) to identify one or more healthcare attributes associated with the healthcare service. Alternatively, ML model generator may implement an artificial neural network learning algorithm to generate the healthcare attributes model as a neural network that is an interconnected group of artificial neurons. The neural network may be presented with information related to the request for a healthcare service to identify healthcare attributes associated with the requested healthcare service.

In some embodiments, healthcare attribute engine 404 may determine healthcare attributes associated with the healthcare service by applying information associated with a request for coverage of the healthcare service to the healthcare attributes model. Healthcare attribute engine 404 may receive, from the healthcare attributes model, an indication of the healthcare attributes. In some embodiments, healthcare attribute engine 404 may update the healthcare attributes model to account for one or more associations detected between a healthcare attribute and other healthcare attributes.

In some embodiments, healthcare attribute engine 404 may store the one or more healthcare attributes 422 in storage device 420 for healthcare transaction processing engine 408 to access. Healthcare transaction processing engine 408 may receive the one or more healthcare attributes 422 from storage device 420. Healthcare transaction processing engine 408 may be further configured to generate a response 428 to the request for coverage of the service under the health insurance plan based on the one or more healthcare attributes 422. To help illustrate, and with continued reference to the example described above, healthcare transaction processing engine 408 may compare a value of the plan price attribute to a value of the cash price attribute and generate response 428 indicating the value of the price attribute that is less than the value of the other price attribute (such as the value of the cash price attribute if the cash price is less than the plan price).

To help further illustrate, and with continued reference to the example described above regarding drug utilization review, healthcare attribute engine 404 may store the one or more healthcare attributes 422 related to the drug utilization review in storage device 420 for healthcare transaction processing engine 408 to access. For example, healthcare attributes 422 may include the results of the drug utilization review including information on any contraindications with a drug based on a patient's medical history. Healthcare transaction processing engine 408 may be further configured to generate a response 428 to the request for coverage of the service under the health insurance plan based on the results of the drug utilization review.

In some embodiments, healthcare attribute engine 404 may determine one or more healthcare attributes associated with a service received by a member of a health insurance plan based on prefilled popular data 426 stored in storage device 418. Prefilled popular data 426 may be common attributes associated with a healthcare service provided to a patient. For example, in the context of pharmacy claim adjudication, healthcare attribute engine 404 may determine pricing attributes including a price plan and a cash price for filling a prescription based on popular combinations of pharmacy attributes (e.g., drug, pharmacy, quantity, and data supply). In some embodiments, healthcare attribute cache builder 430 may be configured to determine popular combinations of healthcare data and store the popular combinations of healthcare data 426 in storage device 418.

Figure 5:
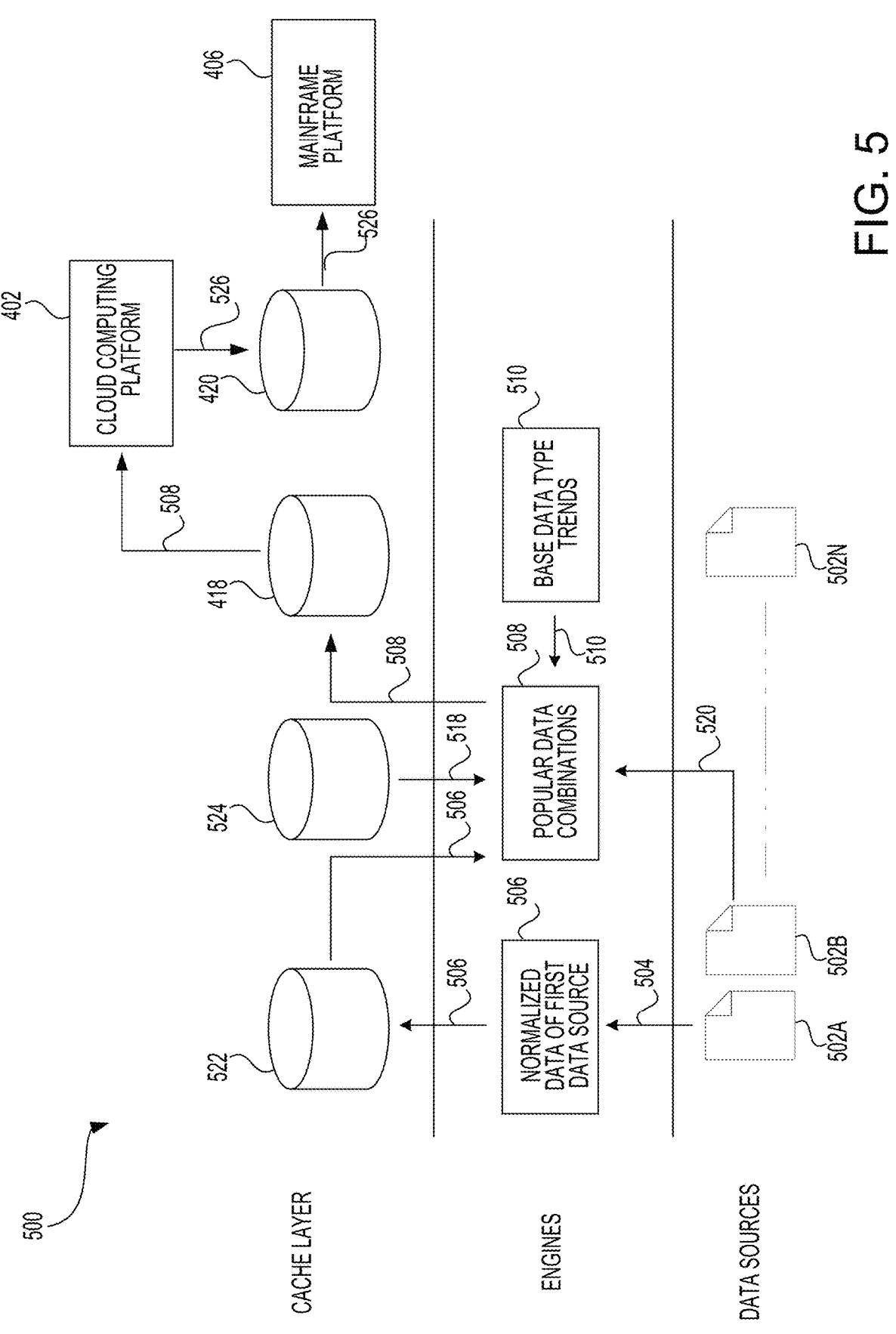
FIG. 5 generally illustrates a functional block diagram of a system for processing healthcare transactions according to the principles of the present disclosure.

To help explore the foregoing in more detail, FIG. 5 will now be described. FIG. 5 is a block diagram of an example implementation of a system 500 for generating and using data stored in storage devices 418 and 420 of FIG. 4. While the system 500 will namely be described within the context of pharmacy claims adjudication, the system 500 and/or components of the system 500 may otherwise be deployed for processing other healthcare transactions. As shown in FIG. 5, system 500 includes storage devices 522 and 524 and storage devices 418 and 420 as depicted in FIG. 4.

As portrayed in FIG. 5, an engine of system 400 of FIG. 4 (e.g., healthcare transaction processing engine 408) may receive data 504 of first data source 502A, normalize data 504 of first data source 502A, and store normalized data 506 of data 504 of first data source 502A in storage device 522. In addition, the engine may generate popular data combinations 508 based on data 520 of a second data source 502B, normalized data 506, data 518 stored in storage device 524, and base data type trends 510, and store popular data combinations 508 in storage device 418. Cloud computing platform 402 may receive popular data combinations 508 and determine if a combination of popular data combinations 508 exists in data encounters 526. If it does not, then cloud computing platform 402 may store the combination of popular data combinations 508 in storage device 420. Mainframe platform 406 may access data stored in storage device 420.

To help further illustrate, during the adjudication of a pharmacy claim, each pharmacy within a network may have a different price for a drug depending upon the contract between the pharmacy and a health insurance provider. An engine (e.g., a pharmacy network normalization engine) of system 400 or 900 may consolidate different pharmacies in a network into aggregated pharmacies at a chain level (e.g., Walgreens®, CVS Pharmacy®, etc.) so that prices for drugs associated with pharmacies in the network are aggregated into groups at the chain level (e.g., normalized data 506). Additionally, or alternatively, relatively smaller, independent pharmacies may be aggregated into groups based on prices for drugs in contracts between these pharmacies and the health insurance provider. Further, popular script combinations (e.g., drug, pharmacy, quantity, and day supply) may be extracted from historical pharmacy claims (e.g., data 520 of data source 502B) and the aggregated pharmacy chain data, and overlaid with drug National Drug Codes (NDCs) (e.g., data 518). Further, pre-calculated prices for drugs in question may be determined for two data points (such as drug base prices for 7 days or less or 85 days or more (e.g., base data type trends 510)). The popular script combinations (e.g., popular data combinations 508) may be made available to cloud computing platform 402 so that when a pharmacy claim is received different price points can be leveraged by cloud computing platform 402 to provide pricing for drugs being filled in a pharmacy claim to mainframe platform 406. This helps reduce overall processing time of pharmacy claims.

To explore this further, FIG. 6 will now be described. FIG. 6 shows a method 600 for processing healthcare transactions. The method 600 is performed by processing logic that may include hardware (circuitry, dedicated logic, etc.), software (such as is run on a general purpose computer system or a dedicated machine), or a combination of both. The method 600 and/or each of their individual functions, routines, subroutines, or operations may be performed by one or more processors of a computing device (e.g., any component of FIG. 4, such as cloud computing platform 402 and mainframe platform 406). In certain implementations, the method 600 may be performed by a single processing thread. Alternatively, the method 600 may be performed by two or more processing threads, each thread implementing one or more individual functions, routines, subroutines, or operations of the methods.

For simplicity of explanation, the method 600 is depicted and described as a series of operations. However, operations in accordance with this disclosure can occur in various orders and/or concurrently, and with other operations not presented and described herein. For example, the operations depicted in the method 600 may occur in combination with any other operation of any other method disclosed herein. Additionally, or alternatively, not all illustrated operations may be required to implement the method 600 in accordance with the disclosed subject matter. In addition, those skilled in the art will understand and appreciate that the method 600 could alternatively be represented as a series of interrelated states via a state diagram or events.

As shown in FIG. 6, method 600 beings at step 602. At step 602, a request is received for coverage of a service received by a member under a health insurance plan by a cloud computing platform and a mainframe platform. For example, as described with reference to FIG. 4, cloud computing platform 402 and mainframe platform 406 may receive a request (e.g., healthcare transaction 412) for coverage of a service received by a member under a health insurance plan.

At step 604, coverage of the service under the health insurance plan is assessed by the mainframe platform. For example, with continued reference to FIG. 4, mainframe platform 406 may assess coverage of the service under the health insurance plan. More specifically, mainframe platform 406 may determine eligibility of the member under the health insurance plan and in response to determining that the member is eligible under the health insurance plan, determine if the service is covered by the health insurance plan.

A step 606, a first healthcare attribute and a second healthcare attribute associated with the service is determined by the cloud computing platform. For example, with continued reference to FIG. 4 cloud computing platform 402 may determine a first healthcare attribute and a second healthcare attribute (e.g., healthcare attributes 422) associated with the service.

A step 608, the first healthcare attribute and the second healthcare attribute is received by the mainframe platform. For example, with continued reference to FIG. 4, mainframe platform 406 may receive the first healthcare attribute and the second healthcare attribute (e.g., healthcare attributes 422) in response to determining that the service is covered by the health insurance plan.

A step 610, a response is generated to the request for coverage of the service under the health insurance plan indicating the value associated with the second healthcare attribute by the mainframe platform. The response is generated in response to a value associated with the first healthcare attribute being greater than a value associated with the second healthcare attribute. For example, with continued reference to FIG. 4, mainframe platform 406 may generate a response (e.g., response 428) to the request for coverage of the service under the health insurance plan indicating the value associated with the second healthcare attribute (e.g., healthcare attributes 422). The response may be generated in response to a value associated with the first healthcare attribute (e.g., healthcare attributes 422) being greater than a value associated with the second healthcare attribute.

Figure 7:
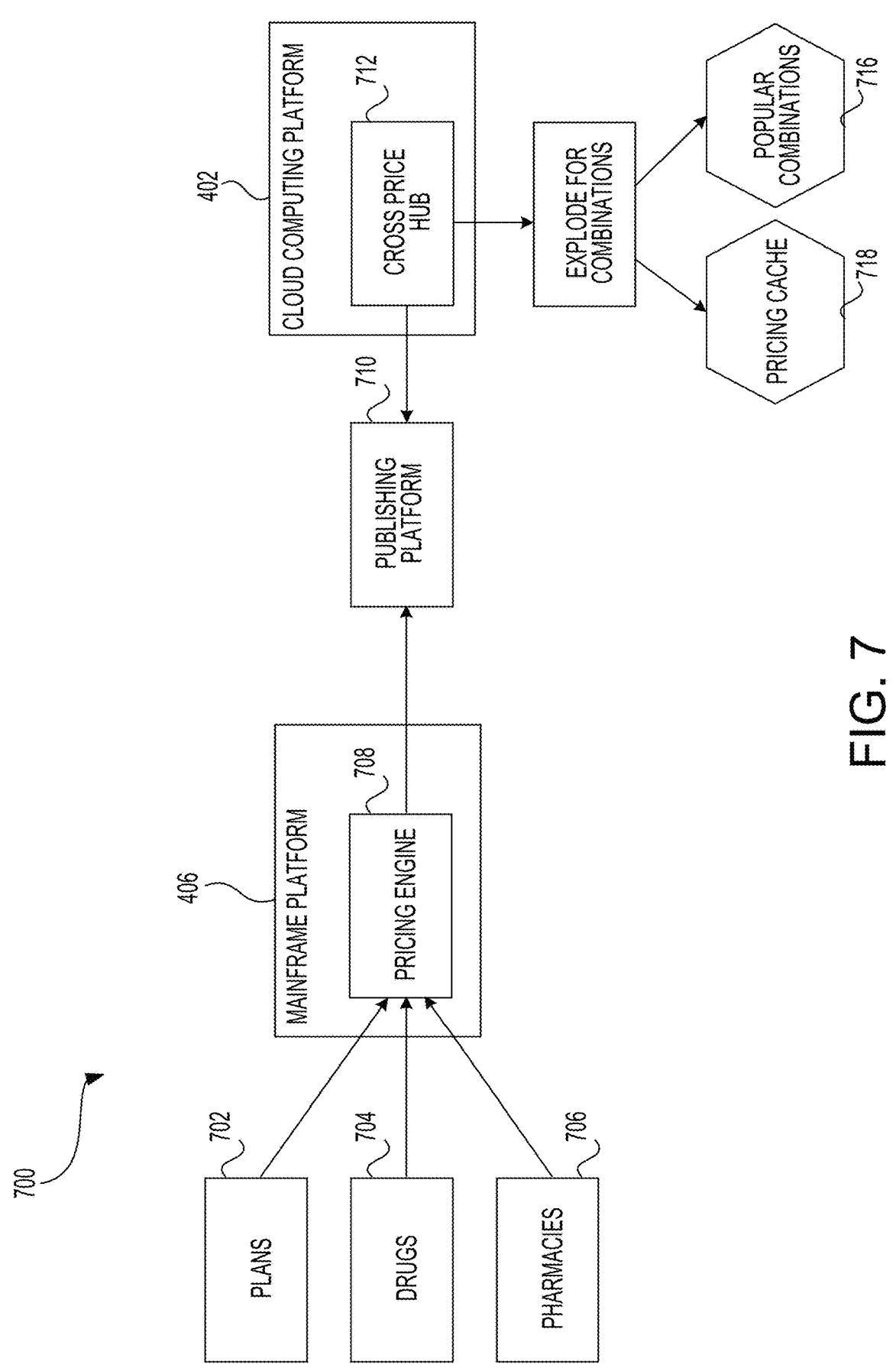
FIG. 7 generally illustrates block diagram of an example implementation of a system for building a pricing cache according to the principles of the present disclosure.

FIG. 7 will now be described. FIG. 7 is a block diagram of an example implementation of a system 700 for building a pricing cache. While the system 700 will be described within the context of pharmacy claims adjudication, the system 700 and/or components of the system 700 may otherwise be deployed for processing other healthcare transactions. As shown in FIG. 7, system 700 includes a pricing engine 708 of mainframe platform 406 and a cross price hub 712. Pricing engine 708 is an exemplary embodiment of healthcare transaction processing engine 408 in FIG. 4, and cross price hub 712 is an exemplary embodiment of healthcare attribute engine 404 in FIG. 4.

Initially, as resented in FIG. 7, pricing engine 708 of mainframe platform 406 receives a healthcare plan design (such as pricing parameters of the healthcare plan) and information related to pharmacies and drugs. Results, which include combinations of drugs and pharmacies, of pricing engine 708 may be published to a publishing platform 710 (e.g., Kafka topics) and the results may be consumed by cross price hub 712 of cloud computing platform 402. Cross price hub 712 may explode the results of combinations of drugs and pharmacies into multiple combinations 716 of drug day supply and drug quantity. The multiple combinations 716 may be stored in a storage device (e.g., storage device 418 in FIG. 4 and FIG. 5). The storage device of popular combinations may store all known encounters of a drug quantity and daily supply associated with a drug. Cross price hub 712 may further create a pricing cache 718 of all known pricing combinations of the multiple combinations 716. If something changes (e.g., health insurance pricing formula changes, pharmacy contract changes, drug price changes, etc.), the changes can be incorporated dynamically and in real time to this process. In some embodiments, system 700 may sense changes that influence pricing and make necessary adjustments. Still yet, in some embodiments, system 700 can generate clinically compatible drug quantities, which are strategic values that can extrapolate linearly to generate any quantity and day supply results.

Figure 8:
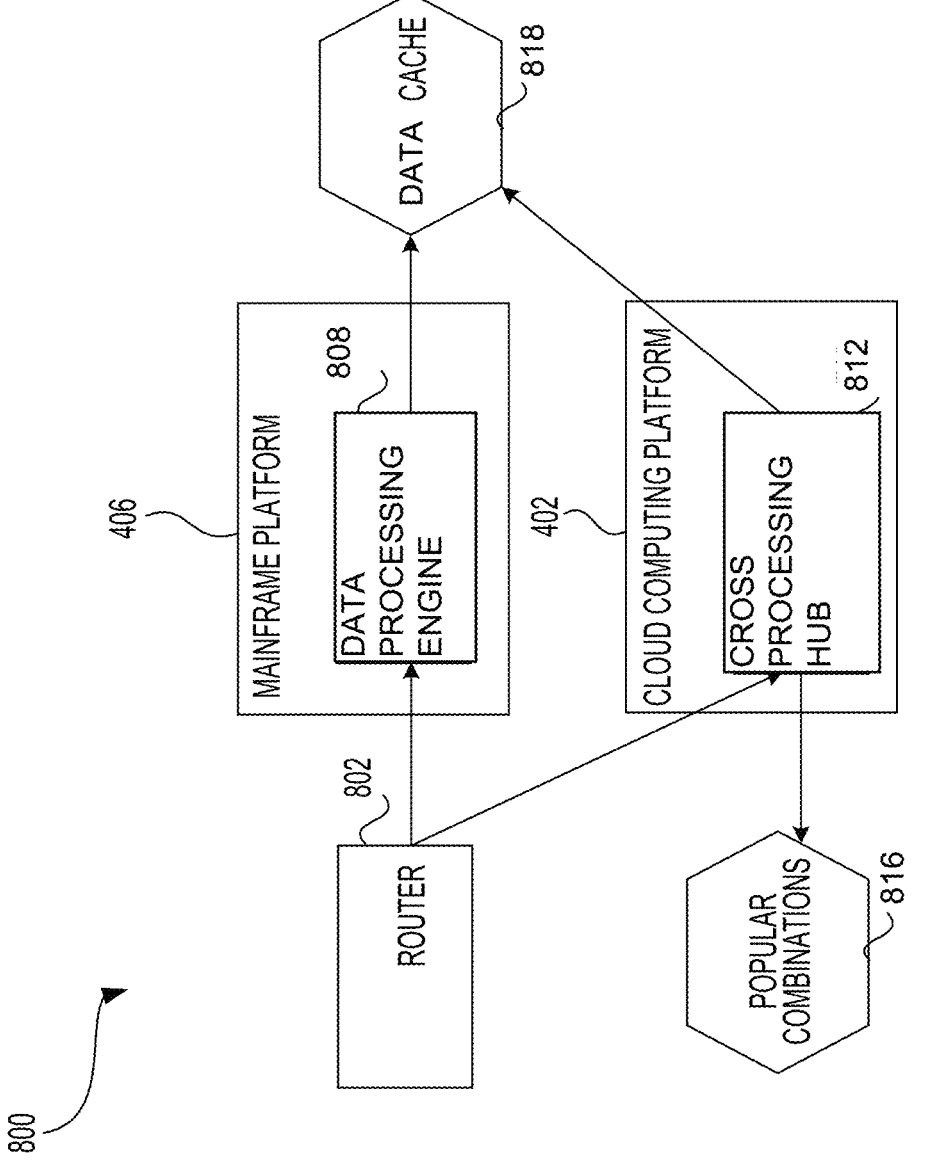
FIG. 8 generally illustrates block diagram of an example implementation of a system for using a data cache according to the principles of the present disclosure.

FIG. 8 will now be described. FIG. 8 is a block diagram of an example implementation of a system 800 for using a data cache. While the system 800 will be described within the context of data processing, e.g., pharmacy claims adjudication, the system 800 and/or components of the system 800 may otherwise be deployed for processing other healthcare transactions such as medical claims, dental claims and the like. The system 800 can also be used to apply the subset of rules to generate a combination record to use parallel data approval requests based on the generated database in one path and apply another subset of rules to approve requests based on a look up database.

Initially, as represented in FIG. 8, a data processing request is received by a router 802 and the claim is provided to pricing data processing engine 808 (e.g., a normal processing path or adjudication path) and a cross processing hub 812. The data processing request may can include a data record. The data record can include the source of the data record, an identifier of a set of data processing rules, an identifier of the subject of the request, and other data required to process the data request. In some embodiments, the data processing request may be asynchronously passed to cross processing hub 812. Cross processing hub 812 may validate if the data processing request, e.g., a claim data record in some embodiments, may be serviced by existing results based on popular combinations 816 (e.g., determining whether an attribute for the data record have been pre-calculated, such as part of a model). If not, cross processing hub 812 adds the scenario to the popular combinations 816 and inserts the new data to the data cache 818. For example, assume for illustration purposes a data request is received for an action that normally has a first attribute, e.g., dosage, quantity, frequency, strength, provider, or the like. However, the data record has the first attribute that does not agree with a second attribute. The cross processing hub 812 may dynamically calculate two results for the data record based upon both the first attribute and the second attribute. The cross processing hub 812 can then publish the first result and the second result to the data cache 818. For example, additionally assume for illustration purposes a data request is received for a prescription for a drug that is normally prescribed for a ninety-day supply and taken once a day for a quantity of ninety. However, the prescription for the drug is for a ninety-day supply and a quantity of one hundred eighty. Cross processing hub 812 may dynamically calculate the price for the drug based upon the ninety-day supply and quantity of one hundred eighty attributes and publish the price to data cache 818.

Figure 9:
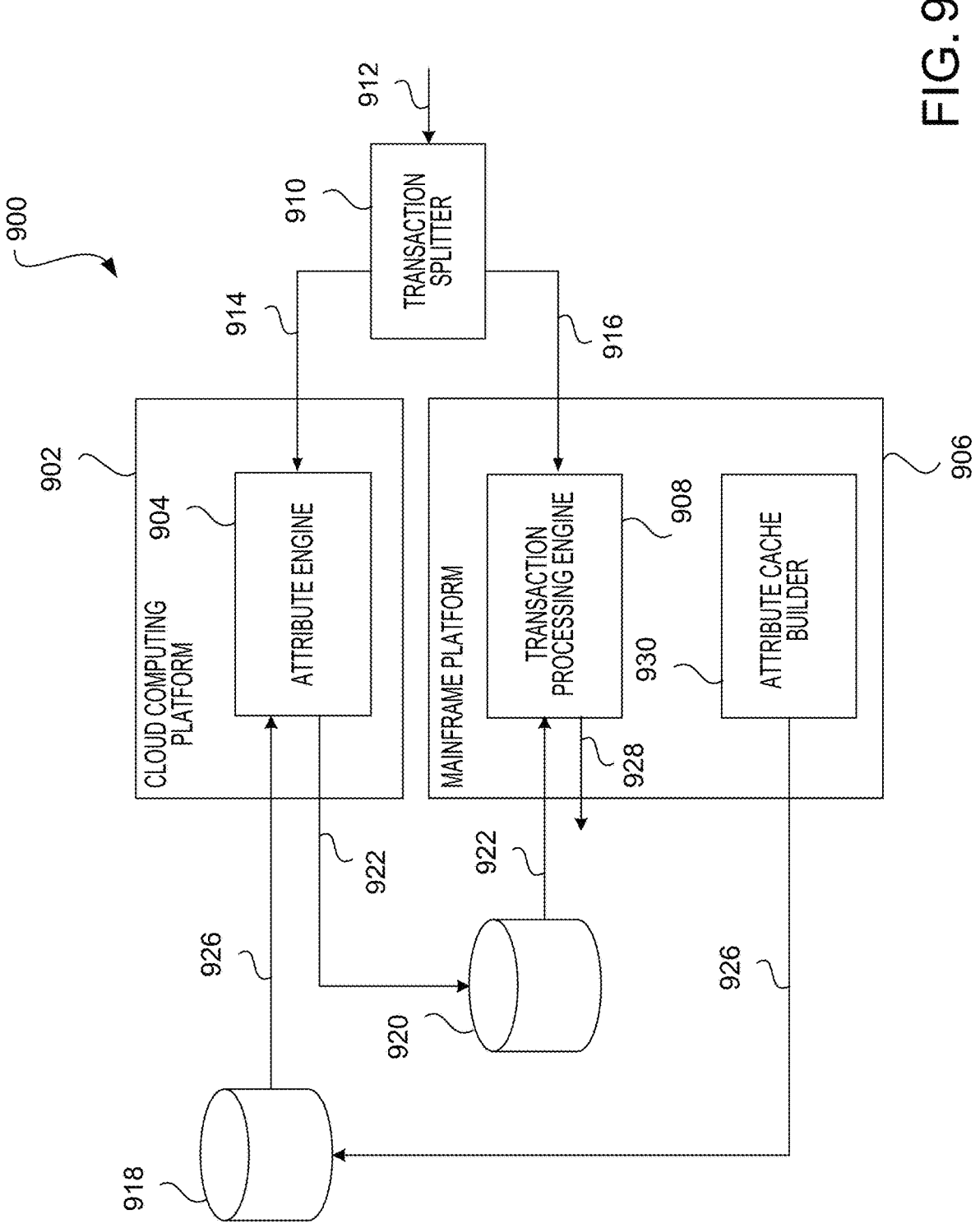
FIG. 9 generally illustrates a functional block diagram of a system for processing data transactions according to the principles of the present disclosure.

FIG. 9 is a block diagram of an example implementation of a system 900 for processing data processing requests. In accordance with embodiments described herein, select workloads may be performed on the cloud computing platform rather than on the mainframe platform such that aspects of the data processing can be processed in parallel. As shown in FIG. 9, system 900 includes a cloud computing platform 902, a mainframe platform 906, a data processing splitter 910, and storage devices 918 and 920. As further shown in FIG. 9, cloud computing platform 902 includes an attribute engine 904, and a mainframe platform 906 includes a processing engine 908 and an attribute cache builder 930.

A processing transaction splitter 910 may be configured to receive a data processing transaction request 912 and provide a data record 916 associated with data processing transaction request 912 to a data transaction processing engine 908 and a data record 914 associated with the data processing transaction request 912 to an attribute engine 904. For example, the data processing transaction request 912 may include a data record for requesting data processing using a set of rules (e.g., healthcare service, dental care, a doctor visit, laboratory work, diagnostic care, security clearance, ownership, authentication, ordering, etc.) provided to a specific member under governance of the rule set. More specifically, in the context of ordering, the transaction splitter 910 may receive an order record 912 requesting eligibility for a member under the rule set and provide the rule set and/or certain attributes of the order (e.g., quantity, type, color, legality, or the like) to the transaction processing engine 908 and the attribute engine 904.

In FIG. 9, the transaction processing engine 908 may be configured to receive data 916 associated with the transaction request 912 and the process data 916 to assess eligibility of the service under the rule set. To help further illustrate, and with continued reference to the examples described herein, the transaction processing engine 908 may be configured to receive the pharmacy claim and assess coverage of a drug under the health insurance plan (e.g., verifying eligibility for the member, performing a drug utilization review (DUR) for the member, etc.).

Further, the attribute engine 904 may be configured to receive data 914 associated with processing transaction request 912 and processing data 914 to determine one or more associated attributes associated with a service received by member of a scheme covered by the rule set. To help illustrate, and with continued reference to the example described herein, the attribute engine 904 may receive a data processing request for a member under a rule set and determine one or more attributes associated with service for the member. The attributes can be vectors or variables input in the data processing but are not specifically part of the data processing request 912. For example, the attributes may include a first input for filling the prescription under the health insurance plan and a second price for filling the prescription without using the health insurance plan. In some embodiments, the attribute engine 904 may be responsible for performing the pricing aspect of the pharmacy claim adjudication in parallel with the necessary health insurance coverage checks performed by transaction processing engine 908.

In some embodiments, the attribute engine 904 may be configured to perform attribute application to the data processing request in parallel with the necessary coverage checks performed by the transaction processing engine 908. For example, the attribute engine 904 may compare an ordered item with member information for possible drawbacks of the member using the items, safety, interactions, or duplicate therapy. The attribute engine 904 and/or the transaction processing engine 908 may be configured to process any aspect of a processing request adjudication. Further, the attribute engine 904 and the transaction processing engine 908 may be configured to process in parallel different aspects of data processing, e.g., claim adjudication.

Additionally, or alternatively, the attribute engine 904 may include a machine learning (ML) model generator and ML models. The ML model generator may be configured to generate the ML models to facilitate determining one or more healthcare attributes associated with a service. The ML models may be deployed in the attribute engine 904.

In some embodiments, the ML model generator may be configured to generate an attribute association model that generates one or more predictions indicating associations between attributes or healthcare attributes. For example, the model generator includes a machine learning algorithm. Machine learning algorithm may be provided with attributes associated with previous requests for services as input and is executed by model generator to generate the attribute association model. The attribute association model may generate predictions indicating associations between attributes associated with data processing services. Some attributes may include member information (e.g., gender, occupation, age, location, etc.), information related to the service (e.g., diagnosis code, place of service, date of service, service code, etc.), and participation information (e.g., subscriber identification number or plan number, deductible, insurance type, participation level, etc.).

Additionally, or alternatively, ML model generator may also include a ML application that implements the ML algorithm to the attribute association model. When the ML algorithm is implemented, it may find patterns between the attributes to map the attributes to each other, and output a model that captures the associations between attributes. The attributes model may be generated using any suitable techniques, including supervised machine learning model generation algorithms such as supervised vector machines (SVM), linear regression, logistic regression, naïve Bayes, linear discriminant analysis, decision trees, k-nearest neighbor algorithm, neural networks, recurrent neural network, etc. In some embodiments, unsupervised learning algorithms may be used such as clustering or neural networks.

Note that the attributes model may be generated in various forms. In accordance with some embodiments, the attributes model may be generated according to a suitable machine-learning algorithm mentioned elsewhere herein or otherwise known. In some embodiments, the ML model generator may implement a gradient boosted tree algorithm or other decision tree algorithm to generate and/or train the attributes model in the form of a decision tree. The decision tree may be traversed with input data (information related to the request for a service, etc.) to identify one or more attributes associated with the service and data processing request. Alternatively, ML model generator may implement an artificial neural network learning algorithm to generate the attributes model as a neural network that is an interconnected group of artificial neurons. The neural network may be presented with information related to the request for a healthcare service to identify healthcare attributes associated with the requested data processing service.

In some embodiments, the attribute engine 904 may determine attributes associated with the service by applying information associated with a request for data processing including the attributes model. The attribute engine 904 may receive, from the attributes model, an indication of the attributes. In some embodiments, the attribute engine 904 may update the attributes model to account for one or more associations detected between the attribute and other attributes.

In some embodiments, the attribute engine 904 may store the one or more attributes 922 in storage device 920 for the transaction processing engine 908 to access. The transaction processing engine 908 may receive the one or more attributes 922 from the storage device 920. The transaction processing engine 908 may be further configured to generate a response 928 to the request for coverage of the service under the rule set based at least in part on the one or more attributes 922. To help illustrate, and with continued reference to the examples described herein, the transaction processing engine 908 may compare a value of the rule set attribute to a value of another attribute for an alternative item or service the cash price attribute and generate the response 928 indicating a generated value based on comparison of the attributes. The attributes can represent value to the member of efficiency of service, including data processing.

To help further illustrate, and with continued reference to the example described herein regarding safety review, the attribute engine 904 may store the one or more attributes 922 related to the safety review in storage device 920 for the transaction processing engine 908 to access. For example, the attributes 922 may include the results of the safety review including information on any contraindications with items or services. The transaction processing engine 908 may be further configured to generate a response 928 to the request for services or items under the rule set based on the results of the safety review.

In some embodiments, the attribute engine 904 may determine one or more attributes associated with a service or item received by a member under the rule set can be based on prefilled data 926 stored in storage device 918. Prefilled data 926 may be common attributes associated with a service or an item provided to the member. For example, the common attributes can be based, at least in part, on popular combinations of attributes. In some embodiments, the attribute cache builder 930 may be configured to determine popular combinations of the data and store the popular combinations of the data 926 in storage device 918.

The presently described systems and methods can provide fraud, waste and abuse analysis data when health data relating to treatment and prescriptions is compiled on a global basis, e.g., by processing data requests within a first set of rules and a second set or rules, or by adjudicating prescription drug claims within a health plan or with a discount plan that is part of a health plan adjudication methodology. The data can be compiled and analyzed for fraud, waste and abuse or threats, e.g., by the systems and methods described in co-pending U.S. patent application Ser. No. 15/999,135, filed 17 Aug. 2018, titled DATA INTEGRATION AND PREDICTION FOR FRAUD, WASTE AND ABUSE, which is hereby incorporated by reference for any purpose or in U.S. patent Ser. No. 10/776,890, granted 20 Sep. 2020, titled GENERATION FROM DATA THREATS AND PREDICTIVE APPLICATION OF THE DATA MODELS, which is hereby incorporated by reference for any purpose.

In some embodiments, a system for processing data record transactions can include a cloud computing platform and a mainframe platform. The cloud computing platform that includes at least a first processor and at least a first memory including instructions that, when executed by the first processor, cause the first processor to: train, based on attributes associated with select remote services, a machine learning model that generates one or more predictions indicating associations between the attributes; receive a request for data processing associated with a member under a rule set; determine a first attribute and a second attribute associated with the member. Determining the first attribute and the second attribute includes: applying information associated with the data processing request to the machine learning model; and receiving, from the machine learning model, an indication of the first attribute and the second attribute; and store the first attribute and the second attribute. The mainframe platform can include a second processor and a second memory including instructions that, when executed by the second processor, cause the second processor to: receive the data processing request associated with the member under the rule set; determine eligibility of the member under the rule set; in response to determining that the member is eligible under the rule set, determine if the service is eligible covered by the rule set; in response to determining if the service is covered by the rule set, receive the first attribute and the second attribute; and in response to a value associated with the first attribute being greater than a value associated with the second attribute, generate a response to the request for coverage of the service under the rule set indicating the value associated with the second attribute.

In some embodiments, a system for processing healthcare transactions, the system comprises: a cloud computing platform that includes at least a first processor and at least a first memory including instructions that, when executed by the first processor, cause the first processor to: train, based on healthcare attributes associated with healthcare services, a machine learning model that generates one or more predictions indicating associations between the healthcare attributes; receive a request for coverage of a healthcare service received by a member under a health insurance plan; determine a first healthcare attribute and a second healthcare attribute associated with the healthcare service, wherein determining the first healthcare attribute and the second healthcare attribute includes: applying information associated with the request for coverage of the healthcare service to the machine learning model; and receiving, from the machine learning model, an indication of the first healthcare attribute and the second healthcare attribute; and store the first healthcare attribute and the second healthcare attribute;

and a mainframe platform comprising a second processor and a second memory including instructions that, when executed by the second processor, cause the second processor to: receive the request for coverage of the healthcare service received by the member under the health insurance plan; determine eligibility of the member under the health insurance plan; in response to determining that the member is eligible under the health insurance plan, determine if the healthcare service is covered by the health insurance plan; in response to determining if the healthcare service is covered by the health insurance plan, receive the first healthcare attribute and the second healthcare attribute; and in response to a value associated with the first healthcare attribute being greater than a value associated with the second healthcare attribute, generate a response to the request for coverage of the healthcare service under the health insurance plan indicating the value associated with the second healthcare attribute.

In some embodiments, the second memory further includes instructions that, when executed by the second processor, cause the second processor to: in response to the value associated with the first healthcare attribute being less than the value associated with the second healthcare attribute, generate the response to the request for coverage of the healthcare service under the health insurance plan indicating the value associated with the first healthcare attribute.

In some embodiments, the healthcare service is associated with filling a prescription for a drug.

In some embodiments, the first healthcare attribute includes a price for the healthcare service under the health insurance plan and the second healthcare attribute includes a price for the healthcare service without using the health insurance plan.

In some embodiments, the second memory further includes instructions that, when executed by the second processor, cause the second processor to: determine popular combinations of healthcare data based on historical health insurance claims.

In some embodiments, the first memory further includes instructions that, when executed by the first processor, cause the first processor to: determine the first healthcare attribute and the second healthcare attribute based on the popular combinations of healthcare data.

In some embodiments, the first memory further includes instructions that, when executed by the first processor, cause the first processor to: update the machine learning model to account for one or more associations detected between the first healthcare attribute and the second healthcare attribute and between the first healthcare attribute and the second healthcare attribute with other healthcare attributes.

In some embodiments, the first memory further includes instructions that, when executed by the first processor, cause the first processor to: determine whether the mainframe platform has access to attributes associated with the healthcare service.

In some embodiments, the first memory further includes instructions that, when executed by the first processor, cause the first processor to: in response to determining the mainframe platform does not have access to attributes associated with the healthcare service: determine the first healthcare attribute and the second healthcare attribute associated with the healthcare service; and store the first healthcare attribute and the second healthcare attribute in a data store for the mainframe platform to access for generating a response to the request for coverage of the healthcare service.

In some embodiments, a method performed by a system for processing healthcare transactions, the system comprising a cloud computing platform and a mainframe platform, and the method comprising: training, based on healthcare attributes associated with healthcare services, a machine learning model that generates one or more predictions indicating associations between the healthcare attributes; receiving, by the cloud computing platform and the mainframe platform, a request for coverage of a healthcare service received by a member under a health insurance plan; determining, by the mainframe platform, eligibility of the member under the health insurance plan, wherein determining the first healthcare attribute and the second healthcare attribute includes: applying information associated with the request for coverage of the healthcare service to the machine learning model; and receiving, from the machine learning model, an indication of the first healthcare attribute and the second healthcare attribute; and; in response to determining that the member is eligible under the health insurance plan, determining, by the mainframe platform, if the healthcare service is covered by the health insurance plan; determining, by the cloud computing platform, a first healthcare attribute and a second healthcare attribute associated with the healthcare service; in response to determining that the healthcare service is covered by the health insurance plan, receiving, by the mainframe platform, the first healthcare attribute and the second healthcare attribute; and generating, by the mainframe platform, a response to the request for coverage of the healthcare service under the health insurance plan indicating a value associated with the second healthcare attribute, wherein the response is generated in response to a value associated with the first healthcare attribute being greater than a value associated with the second healthcare attribute.

In some embodiments, the method further comprises: in response to the value associated with the first healthcare attribute being less than the value associated with the second healthcare attribute, generating the response to the request for coverage of the healthcare service under the health insurance plan indicating the value associated with the first healthcare attribute.

In some embodiments, the healthcare service is associated with filling a prescription for a drug.

In some embodiments, the first healthcare attribute includes a price for the healthcare service under the health insurance plan and the second healthcare attribute includes a price for the healthcare service without using the health insurance plan.

In some embodiments, the method further comprises determining popular combinations of healthcare data based on historical health insurance claims.

In some embodiments, the method further comprises determining the first healthcare attribute and the second healthcare attribute based on the popular combinations of healthcare data.

In some embodiments, the method further comprises: determining whether the mainframe platform has access to attributes associated with the healthcare service.

In some embodiments, the method further comprises: in response to determining the mainframe platform does not have access to attributes associated with the healthcare service: determining the first healthcare attribute and the second healthcare attribute associated with the healthcare service; and storing the first healthcare attribute and the second healthcare attribute in a data store.

In some embodiments, a system for processing healthcare transactions, the system comprises: a cloud computing platform that includes at least a processor and at least a first memory including instructions that, when executed by the processor, cause the processor to: train, based on healthcare attributes associated with healthcare services, a machine learning model that generates one or more predictions indicating associations between the healthcare attributes; receive a request for coverage of a healthcare service received by a member under a health insurance plan; determine whether a mainframe platform has access to healthcare attributes associated with the healthcare service, wherein determining the first healthcare attribute and the second healthcare attribute includes: applying information associated with the request for coverage of the healthcare service to the machine learning model; and receiving, from the machine learning model, an indication of the first healthcare attribute and the second healthcare attribute; and in response to determining the mainframe platform does not have access to the healthcare attributes associated with the healthcare service: determine a first healthcare attribute and a second healthcare attribute associated with the healthcare service; and store the first healthcare attribute and the second healthcare attribute in a data store for the mainframe platform to access for generating a response to the request for coverage of the healthcare service.

In some embodiments, the healthcare service is associated with filling a prescription for a drug.

In some embodiments, the first healthcare attribute includes a price for the healthcare service under the health insurance plan and the second healthcare attribute includes a price for the healthcare service without using the health insurance plan.

The present disclosure describes various embodiments in a healthcare context, e.g., prescription drug approvals; however, some embodiments are not so limited. Some embodiment can be used where approval of an external request needs to be processed in the real time, e.g., credit card transactions, data integrity requests, and the like.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits and circuitry. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

A mainframe can be the central computing server in a client/server system. The mainframe can have high processing power, memory and storage to support massive data processing operations. In contrast, cloud computing is a distributed architecture of multiple systems (e.g., servers smaller than a mainframe) that may communicate with each other over a network, e.g., Internet, web or other communication channels and standards. In some examples, cloud computing is on-demand and can share hardware resources with other users. This can lead to lower costs of use compared to mainframes which require the ownership of sufficient hardware to exceed the future maximum data processing requirements.

Implementations of the systems, algorithms, methods, instructions, etc., described herein may be realized in hardware, software, or any combination thereof. The hardware may include, for example, computers, intellectual property (IP) cores, application-specific integrated circuits (A SIC s), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

What is claimed is:

1. A system for processing healthcare transactions, the system comprising:

a healthcare transaction splitter configured to:
receive data associated with a healthcare transaction;
provide first data of the healthcare transaction to a cloud computing platform; and
provide second data of the healthcare transaction to a mainframe platform;

a cloud computing platform that includes at least a first processor and at least a first memory including instructions that, when executed by the first processor, cause the first processor to:
generate, using an attribute engine on the cloud computing device and using historical requests for healthcare services, a machine learning model configured to generate one or more predictions indicating associations between healthcare attributes;
train, based on healthcare attributes associated with healthcare services, the machine learning model that generates one or more predictions indicating associations between the healthcare attributes;
receive a request for coverage of a healthcare service under a health insurance plan, wherein the request for coverage is associated with the healthcare transaction and corresponds to a member;
determine a first healthcare attribute and a second healthcare attribute associated with the healthcare service based on at least the first data, wherein determining the first healthcare attribute and the second healthcare attribute includes:
providing the request for coverage of the healthcare service to the machine learning model; and
receiving, from the machine learning model, an indication of the first healthcare attribute and the second healthcare attribute; and
store the first healthcare attribute and the second healthcare attribute; and the mainframe platform comprising a second processor and a second memory including instructions that, when executed by the second processor, cause the second processor to:
receive the request for coverage of the healthcare service under the health insurance plan, wherein the request for coverage is associated with the healthcare transaction;

determine eligibility of the member under the health insurance plan;

in response to determining that the member is eligible under the health insurance plan, determine, based on at least the second data, if the healthcare service is covered by the health insurance plan;

in response to determining if the healthcare service is covered by the health insurance plan, receive the first healthcare attribute and the second healthcare attribute; and in response to a value associated with the first healthcare attribute being greater than a value associated with the second healthcare attribute, generate a response to the request for coverage of the healthcare service under the health insurance plan indicating the value associated with the second healthcare attribute; and subsequently train, by the attribute engine on the cloud computing platform, the machine learning model using a k-nearest neighbor algorithm and based on identified associations (i) between the first healthcare attribute and the second healthcare attribute, and (ii) between at least one other healthcare attribute and at least one of the first healthcare attribute and the second healthcare attribute, wherein the attribute engine outputs the subsequently trained machine learning model.

2. The system of claim 1, wherein the second memory further includes instructions that, when executed by the second processor, cause the second processor to:

in response to the value associated with the first healthcare attribute being less than the value associated with the second healthcare attribute, generate the response to the request for coverage of the healthcare service under the health insurance plan indicating the value associated with the first healthcare attribute.

3. The system of claim 1, wherein the healthcare service is associated with filling a prescription for a drug.

4. The system of claim 1, wherein the first healthcare attribute includes a price for the healthcare service under the health insurance plan and the second healthcare attribute includes a price for the healthcare service without using the health insurance plan.

5. The system of claim 1, wherein the second memory further includes instructions that, when executed by the second processor, cause the second processor to:

determine combinations of healthcare data based on historical health insurance claims.

6. The system of claim 5, wherein the first memory further includes instructions that, when executed by the first processor, cause the first processor to:

determine the first healthcare attribute and the second healthcare attribute based on the combinations of healthcare data.

7. The system of claim 1, wherein the first memory further includes instructions that, when executed by the first processor, cause the first processor to:

determine whether the mainframe platform has access to attributes associated with the healthcare service.

8. The system of claim 7, wherein the first memory further includes instructions that, when executed by the first processor, cause the first processor to:

in response to determining the mainframe platform does not have access to attributes associated with the healthcare service:

determine the first healthcare attribute and the second healthcare attribute associated with the healthcare service; and store the first healthcare attribute and the second healthcare attribute in a data store for the mainframe platform to access for generating a response to the request for coverage of the healthcare service.

9. A method performed by a system for processing healthcare transactions, the system comprising a cloud computing platform and a mainframe platform, and the method comprising:

receiving, at a healthcare transaction splitter, data associated with a healthcare transaction;

providing, by the healthcare transaction splitter, first data of the healthcare transaction to the cloud computing platform;

providing, second data of the healthcare transaction to the mainframe platform;

generating, using an attribute engine on the cloud computing platform and using historical requests for healthcare services, a machine learning model configured to generate one or more predictions indicating associations between healthcare attributes;

training, based on healthcare attributes associated with healthcare services, the machine learning model that generates one or more predictions indicating associations between the healthcare attributes;

receiving a request for coverage of a healthcare service under a health insurance plan, wherein the request for coverage is associated with the healthcare transaction and corresponds to a member;

determining, by the mainframe platform, eligibility of the member under the health insurance plan based on a first healthcare attribute and a second healthcare attribute, of the healthcare attributes, by:

providing, at the cloud computing platform, the request for coverage of the healthcare service to the machine learning model; and receiving, by the mainframe platform and from the machine learning model generated by the attribute engine of the cloud computing device, an indication of the first healthcare attribute and the second healthcare attribute, wherein the first healthcare attribute and the second healthcare attribute are determined based on at least the first data; and in response to determining that the member is eligible under the health insurance plan, determining, by the mainframe platform and based on at least the second data, if the healthcare service is covered by the health insurance plan;

in response to determining that the healthcare service is covered by the health insurance plan, receiving, by the mainframe platform, the first healthcare attribute and the second healthcare attribute;

generating, by the mainframe platform, a response to the request for coverage of the healthcare service under the health insurance plan indicating a value associated with the second healthcare attribute, wherein the response is generated in response to a value associated with the first healthcare attribute being greater than a value associated with the second healthcare attribute; and subsequently training, by the attribute engine on the cloud computing platform, the machine learning model using a k-nearest neighbor algorithm and based on identified associations (i) between the first healthcare attribute and the second healthcare attribute, and (il between at least one other healthcare attribute and at least one of the first healthcare attribute and the second healthcare attribute, wherein the attribute engine outputs the subsequently trained machine learning model.

10. The method of claim 9, further comprising:

in response to the value associated with the first health-care attribute being less than the value associated with the second healthcare attribute, generating the response to the request for coverage of the healthcare service under the health insurance plan indicating the value associated with the first healthcare attribute.

11. The method of claim 9, wherein the healthcare service is associated with filling a prescription for a drug.

12. The method of claim 9, wherein the first healthcare attribute includes a price for the healthcare service under the health insurance plan and the second healthcare attribute includes a price for the healthcare service without using the health insurance plan.

13. The method of claim 9, further comprising:

determining combinations of healthcare data based on historical health insurance claims.

14. The method of claim 13, further comprising:

determining the first healthcare attribute and the second healthcare attribute based on the combinations of healthcare data.

15. The method of claim 9, further comprising:

determining whether the mainframe platform has access to attributes associated with the healthcare service.

16. The method of claim 15, further comprising:

in response to determining the mainframe platform does not have access to attributes associated with the health-care service:

determining the first healthcare attribute and the second healthcare attribute associated with the healthcare service; and storing the first healthcare attribute and the second healthcare attribute in a data store.

* * * * *